United States Patent
Malik et al.

(10) Patent No.: US 10,765,402 B2
(45) Date of Patent: Sep. 8, 2020

(54) AUTOMATIC LATERALITY IDENTIFICATION FOR ULTRASOUND TOMOGRAPHY SYSTEMS

(71) Applicant: QT ULTRASOUND LLC, Novato, CA (US)

(72) Inventors: Bilal Hameed Malik, Novato, CA (US); Mark Wayne Lenox, College Station, TX (US); Nasser Charles Pirshafiey, Thousand Oaks, CA (US); James W. Wiskin, Salt Lake City, UT (US)

(73) Assignee: QT ULTRASOUND LLC, Novato, CA (US)

( * ) Notice: Subject to any disclaimer, the term of this patent is extended or adjusted under 35 U.S.C. 154(b) by 738 days.

(21) Appl. No.: 15/360,486

(22) Filed: Nov. 23, 2016

(65) Prior Publication Data

US 2017/0143304 A1    May 25, 2017

Related U.S. Application Data

(60) Provisional application No. 62/258,847, filed on Nov. 23, 2015.

(51) Int. Cl.
*A61B 8/00* (2006.01)
*A61B 8/08* (2006.01)
(Continued)

(52) U.S. Cl.
CPC .......... *A61B 8/4254* (2013.01); *A61B 5/0075* (2013.01); *A61B 5/0077* (2013.01); *A61B 5/015* (2013.01); *A61B 5/708* (2013.01); *A61B 8/0825* (2013.01); *A61B 8/13* (2013.01); *A61B 8/406* (2013.01); *A61B 8/4263* (2013.01); *A61B 8/4416* (2013.01); *A61B 8/54* (2013.01); *A61B 2562/0252* (2013.01); *A61B 2562/046* (2013.01)

(58) Field of Classification Search
CPC ....... A61B 8/4254; A61B 8/0825; A61B 8/13; A61B 8/406; A61B 8/4263; A61B 8/4416; A61B 8/54; A61B 5/0075; A61B 5/0077; A61B 5/015; A61B 5/708; A61B 2562/0252; A61B 2562/046
See application file for complete search history.

(56) References Cited

U.S. PATENT DOCUMENTS 7,558,367 B1 * 7/2009 Tinwala ................. A61B 6/502
378/37
2003/0228033 A1 * 12/2003 Daniel ................. A61B 5/1038
382/104

(Continued)

*Primary Examiner* — Amelie R Davis
*Assistant Examiner* — John Denny Li
(74) *Attorney, Agent, or Firm* — Talem IP Law, LLP

(57) ABSTRACT

An automated system for selecting patient breast laterality is provided. A position sensor system using force or image sensors is coupled to a scanning bed or seated-type apparatus. Regardless of the size and weight of the patient, the position of patient at the time of scan will not be centered with respect to the center of the scanner. This relative difference in the position will be sensed as a difference in the transducer signal of an image sensor when comparing the right- and left-hand sides of the field of view or will be sensed as a difference in voltage when comparing the right and left-hand side outputs of a circuit using force or pressure sensor.

2 Claims, 6 Drawing Sheets

(51) Int. Cl.
*A61B 8/13* (2006.01)
*A61B 5/00* (2006.01)
*A61B 5/01* (2006.01)

(56) References Cited

U.S. PATENT DOCUMENTS

| | | | | |
|---|---|---|---|---|
| 2009/0134966 | A1* | 5/2009 | Baker | G01L 1/20 |
| | | | | 338/99 |
| 2010/0280375 | A1* | 11/2010 | Zhang | A61B 6/463 |
| | | | | 600/443 |
| 2014/0059770 | A1* | 3/2014 | Williamson | G16H 40/63 |
| | | | | 5/617 |
| 2015/0112151 | A1* | 4/2015 | Muhsin | A61B 5/002 |
| | | | | 600/301 |
| 2016/0169737 | A1* | 6/2016 | Bouhnik | G01T 1/1647 |
| | | | | 250/208.1 |
| 2016/0199696 | A1* | 7/2016 | Uehara | A61B 5/227 |
| | | | | 482/8 |

\* cited by examiner

AUTOMATIC LATERALITY IDENTIFICATION FOR ULTRASOUND TOMOGRAPHY SYSTEMS

CROSS-REFERENCE TO RELATED APPLICATION

This application claims the benefit of Provisional Application Ser. No. 62/258,847, filed Nov. 23, 2015.

BACKGROUND

Ultrasound tomography systems generate image slices of a specific cross-section of a scanned object. In a breast ultrasound tomography system, an operator typically enters a patient's information into a field of a graphical user interface to a software application associated with the breast ultrasound tomography system. One of the data fields manually entered by the operator includes selection of breast laterality. That is, whether the left breast or right breast of the patient is being scanned. This data along with other patient and/or session information (e.g., date and time) may be embedded in the metadata of the images generated by the ultrasound tomography system.

The manual entry of the breast laterality can give rise to errors. In particular, a potential major operator error is incorrect selection of breast laterality at the time of patient scan. Since this information is embedded in the metadata of the respective images, the error can directly impact the outcome of the scan and, therefore, diagnosis.

BRIEF SUMMARY

An automated system for selecting patient breast laterality is provided. A system is described that includes a scanner apparatus on which a patient is to be positioned for ultrasound imaging, the scanner bed having an opening through which a patient's breast can be immersed; a position sensor system; and a computing system coupled to the position sensor system and having software stored thereon that, when executed by a processor of the computing system, directs the computing system to: identify, using input received from the position sensor system, whether a user has more of their body to a left side or a right side of the opening; and assign a breast laterality of a right breast or a left breast to data generated by the ultrasound imaging based on whether the user has more of their body to the left side or the right side of the opening.

In one implementation, the sensor system can include force or pressure sensitive sensors located at sides of the opening through which a patient's breast can be immersed. In one such implementation, the appropriate laterality can be identified through the relative difference in weight detected between the two sides.

In another implementation, the sensor system can include one or more image sensors. In one such implementation, the appropriate laterality can be identified through the difference in the transducer signal of captured images of the right- and left-hand sides of the field of view.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

DETAILED DISCLOSURE

An automated system for selecting patient breast laterality is provided. The automated system can reduce the number of operator dependent tasks during ultrasonic imaging. Advantageously, automatic laterality identification can avoid or at least minimize errors arising from incorrect laterality selection in ultrasound tomography systems.

Figure 1:
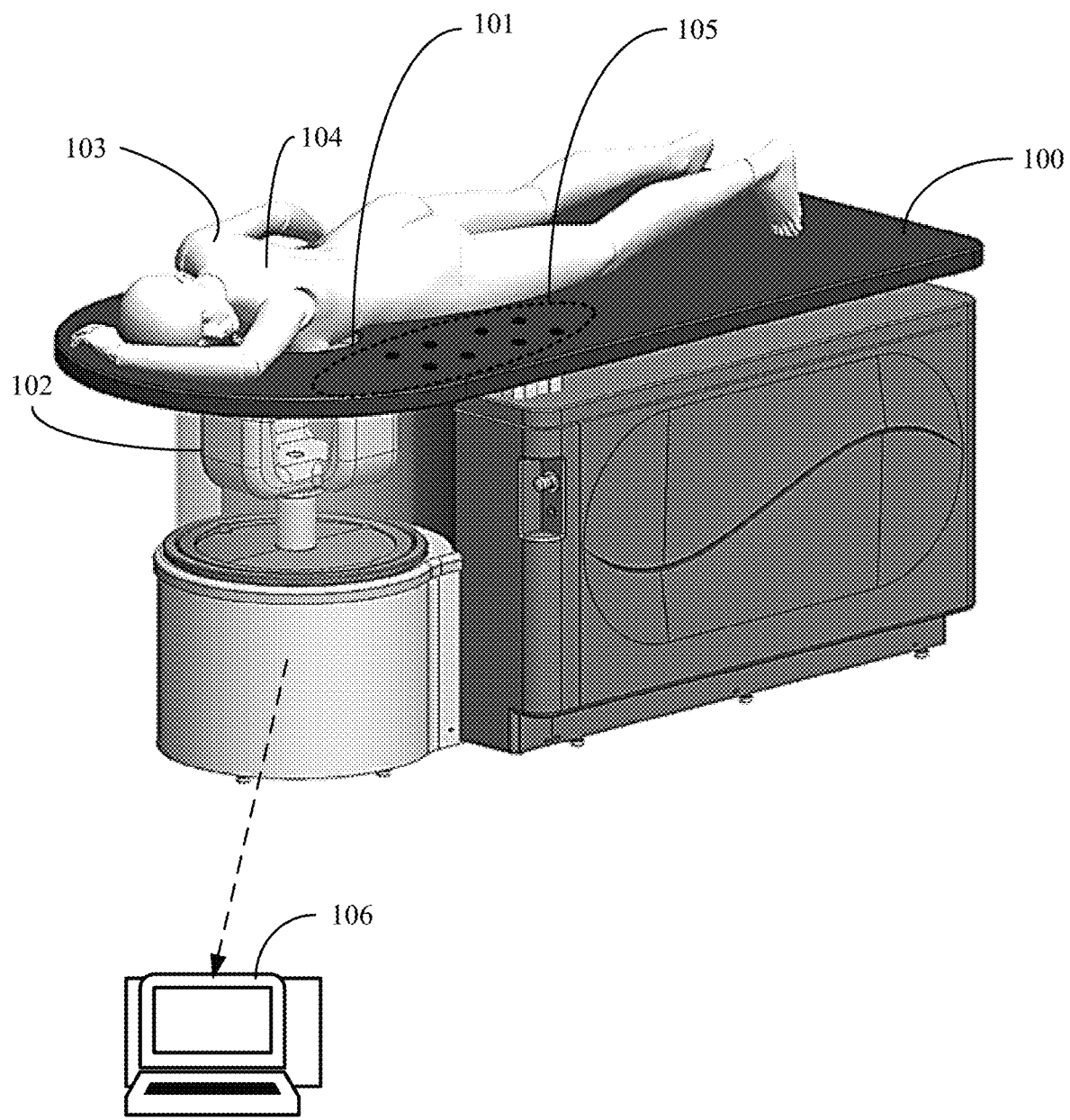
FIG. 1 illustrates an example ultrasound tomography system incorporating breast laterality sensors.
Figure 2A:
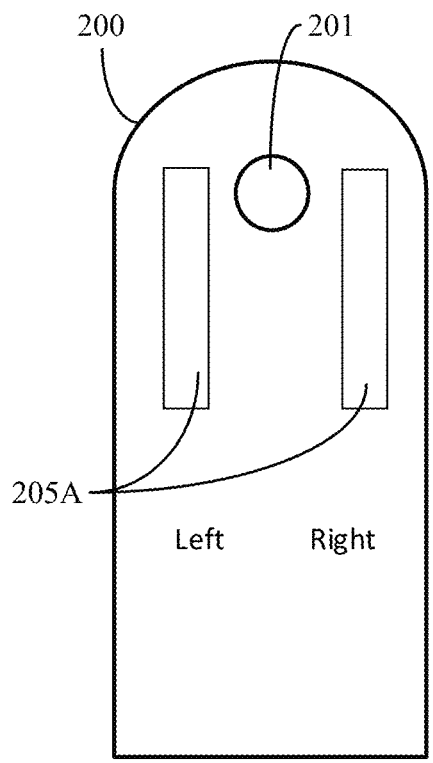
FIGS. 2A-2C illustrate non-limiting example arrangements of breast laterality sensors on a scanning bed.
Figure 2B:
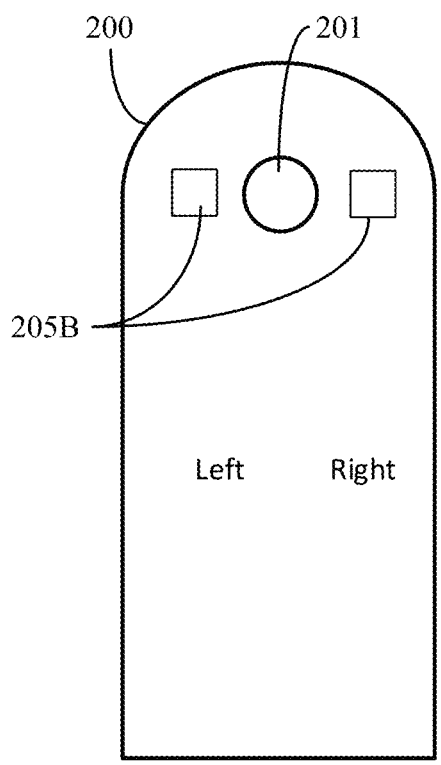
Figure 2C:
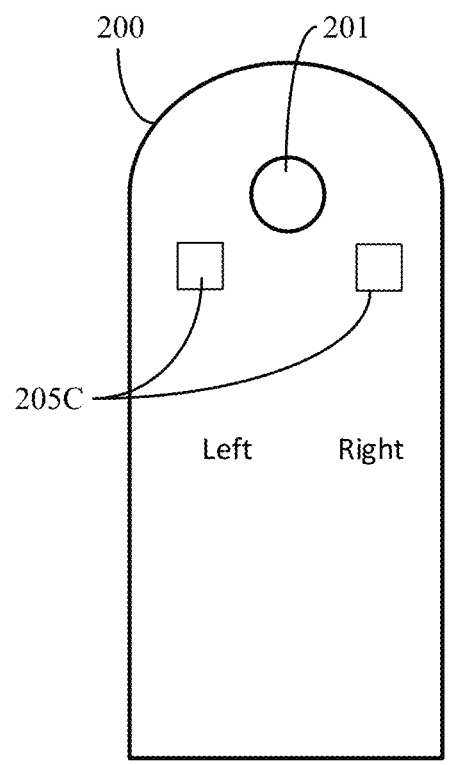

FIG. 1 illustrates an example ultrasound tomography system incorporating breast laterality sensors. Referring to FIG. 1, an ultrasound scanner bed 100 is designed such that positioning of a patient's breast within an opening 101 to the scanner 102 results in relatively non-uniform distribution of weight between the right side 103 and left side 104 of the patient. Pressure sensors 105, such as in the form of force-sensitive resistors, can be arranged on both sides of the bed 100, in configurations such as shown in FIGS. 2A-2C which illustrate non-limiting example arrangements of breast laterality sensors on a scanning bed. For example, a bed 200 can have one or more sensors 205A extending on the bed 200 along a left and right of an opening 201 (see FIG. 2A), can have one or more sensors 205B immediately to the side of the opening 201 (see FIG. 2B), or can have one or more sensors 205C below and to the side of the opening 201 (see FIG. 2C) so that the one or more sensors are at least adjacent the left side of the opening 201 and at least adjacent to the right side of the opening 201.

Returning to FIG. 1, the appropriate laterality can be identified through the relative difference in weight between the two sides of the force-sensitive laterality sensors 105. In this manner, when images are collected from a scan of the patient's breast using the scanner 102, the identified laterality can be used by a computing system 106 associated with the ultrasound tomography system. Indeed, in some cases a session metadata can include the left-right identification generated from the breast laterality sensors.

Figure 3A:
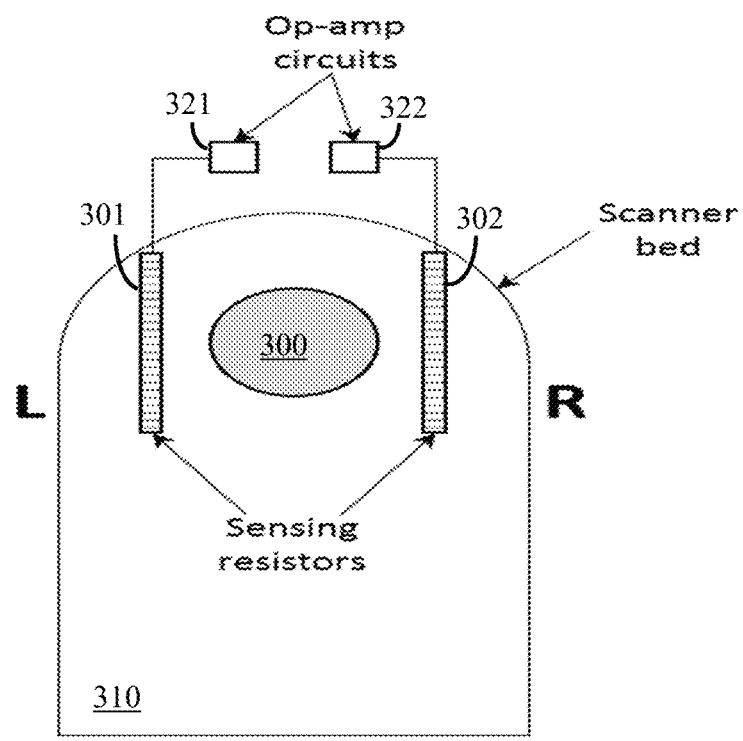
FIGS. 3A and 3B illustrate approximate positioning of resistors on a scanner bed according to example implementations of a sensor system.
Figure 3B:
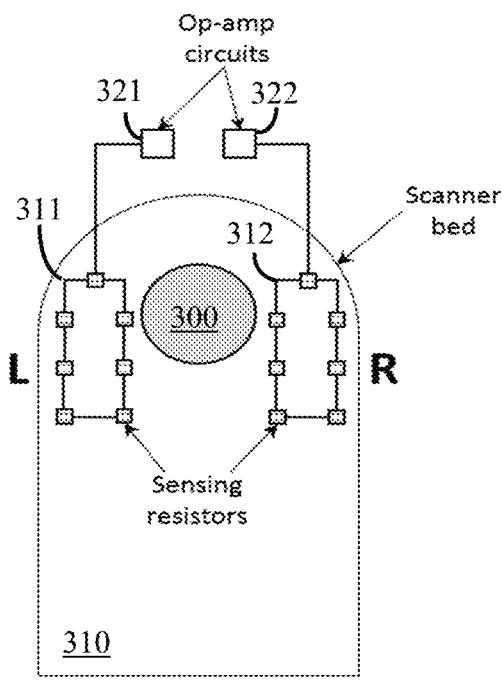
Figure 3C:
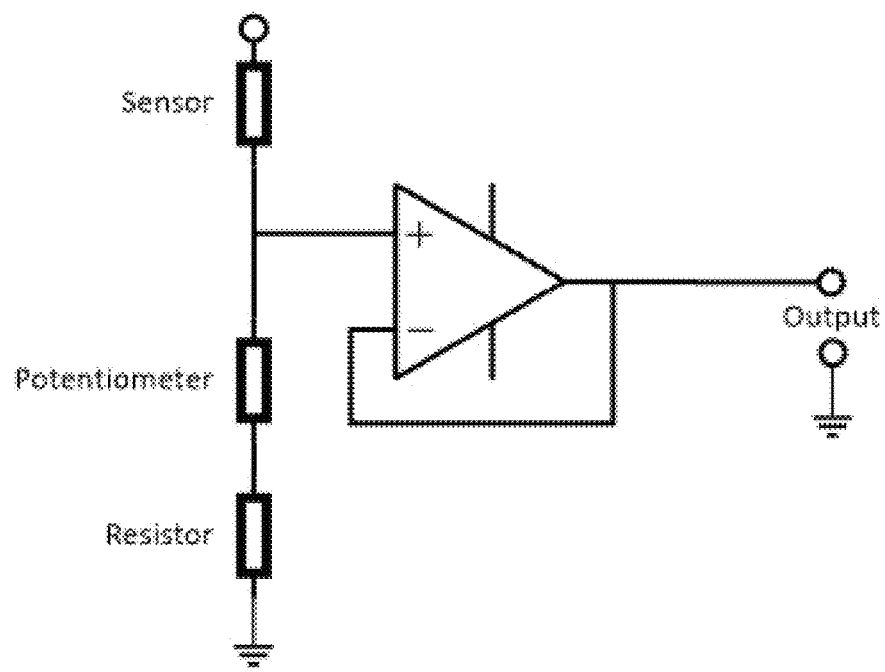
FIG. 3C shows a schematic representation of an op-amp circuit for an example implementation of a sensor system.

FIGS. 3A and 3B illustrate approximate positioning of resistors on a scanner bed according to some example implementations of a sensor system; and FIG. 3C shows a schematic representation of an op-amp circuit for an example implementation of a sensor system. In FIG. 3A, a linear-shaped sensor 301 is provided on the left side of an opening 300 in a scanner bed 310 and another linear-shaped sensor 302 is provided on the right side of the opening 300 in the scanner bed 310. To account for variation in the weight distribution on the scanner bed 310, a network of multiple and smaller resistors can be used in place of the single, linear-shaped sensor 301. For example, such as shown in FIG. 3B, a sensor group 311 of smaller sensors is provided on the left side of the opening 300 in the scanner bed 310; and another sensor group 312 of smaller sensors is provided on the right side of the opening 300 in the scanner bed 310.

Each sensor (301, 302) or sensor group (311, 312) is connected to respective circuit boards 321, 322 of the op-amp circuit represented in FIG. 3C. The output voltage of the op-amp is based on the resistance of the sensor. In FIG. 3C, the sensor (301, 302) or sensor group (311, 312) is represented as an electrical impedance, labeled "Sensor". The sensor(s) may be implemented using force-sensitive resistors. A voltage divider is formed by a resistor and potentiometer connected in series with the sensor and positive node of the op-amp. As reflected by the circuit diagram of FIG. 3C, the circuit is designed such that an increase in force applied to the surface of the left- or right-positioned sensor results in decrease in resistance with a consequent increase in voltage at the output of the op-amp for that corresponding left- or right-positioned sensor.

In the case where the left breast is immersed, through the opening 300, in a water tank (or any type of tank), the left-hand side of the scanner bed 310 experiences slightly less weight in comparison to the right-hand side of the bed 310. In the case where the right breast is immersed, through the opening 300, the right-hand side of the scanner bed 310 experiences slightly less weight in comparison to the left-hand side of the bed 310. This distribution of weight results in a net voltage difference—positive or negative—depending on the breast laterality.

Figure 4:
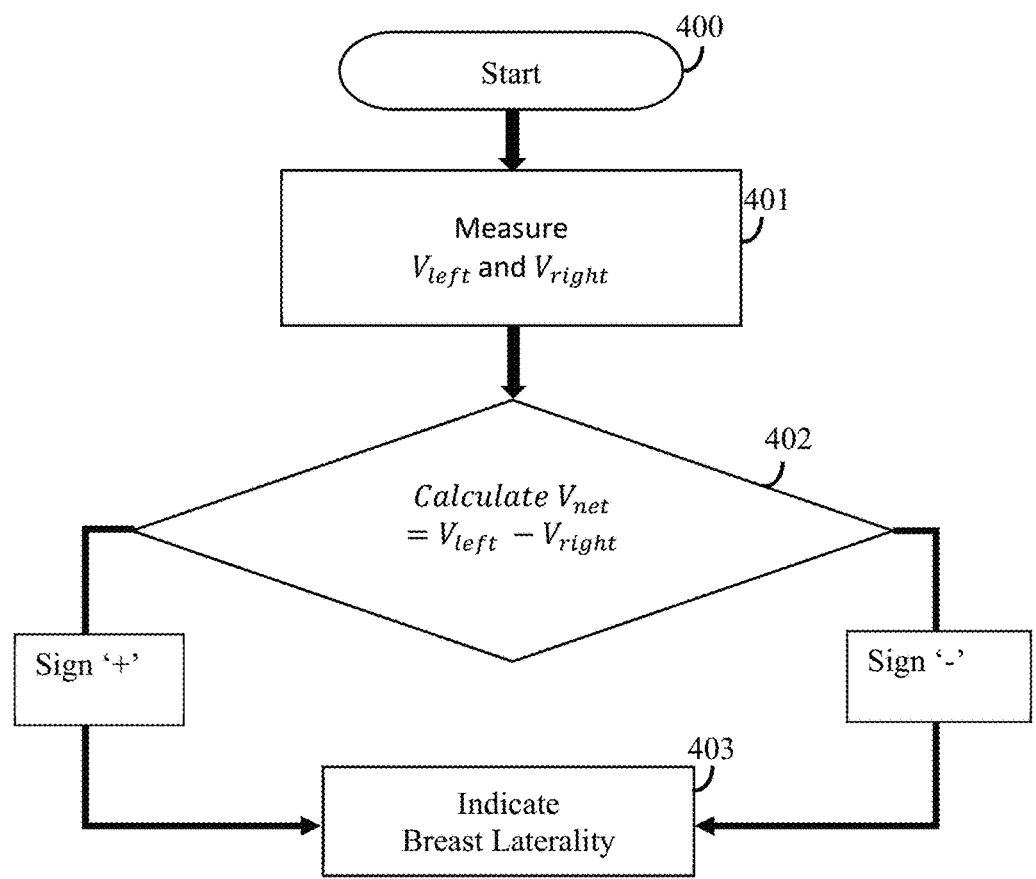
FIG. 4 illustrates a flow chart of an example detection scheme for breast laterality.

FIG. 4 illustrates a flow chart of an example detection scheme for breast laterality. Referring to FIG. 4, the detection scheme 400 can begin by measuring (401) the voltage at the output of the op-amp circuits 321 and 322, which represent the left and the right laterality, and calculating (402) the net difference between the two outputs. The calculation can be $V_{net}=V_{left}-V_{right}$, where $V_{net}$ is the net difference voltage, $V_{left}$ and $V_{right}$ are the output voltages of the left-hand side and rights-hand side sensor circuits, respectively. The breast laterality can be indicated (403) based on this net difference. For example, the decision of breast laterality can be shown by an appropriate indicator such as an LED or on a computer display such as in a graphical user interface of an imaging software associated with the ultrasound tomography system. Note, in this implementation, that the absolute value of the voltage difference is not important for detection of laterality, it is the sign of the difference (sign + or sign −) which determines the decision (a corresponding indication of breast laterality). In some cases, instead of sign, a digital output, such as '0' or '1', can be provided. It should be understood that the net difference may be calculated as $V_{right}-V_{left}$ as long as the system understands how to interpret the output (e.g., can interpret the sign or the digital output as being the appropriate side).

A force-sensitive laterality sensor such as described above is not the only method to measure the relative difference in the position of the patient. For example, in some cases, such as for a seated-style or a standing-style scanner, force sensors may not be as useful. Accordingly, in various implementations for bed-type, seated-type, and standing-type systems, laterality sensing may be carried out by using a vision system (e.g. a charge-coupled device (CCD) or a complementary metal oxide semiconductor (CMOS) camera), an infrared (IR) imager/sensor, an ultrasonic sensor, a thermal sensor/imager, or a combination thereof. These examples of breast laterality sensors may be considered "non-force-sensitive sensors".

Figure 5A:
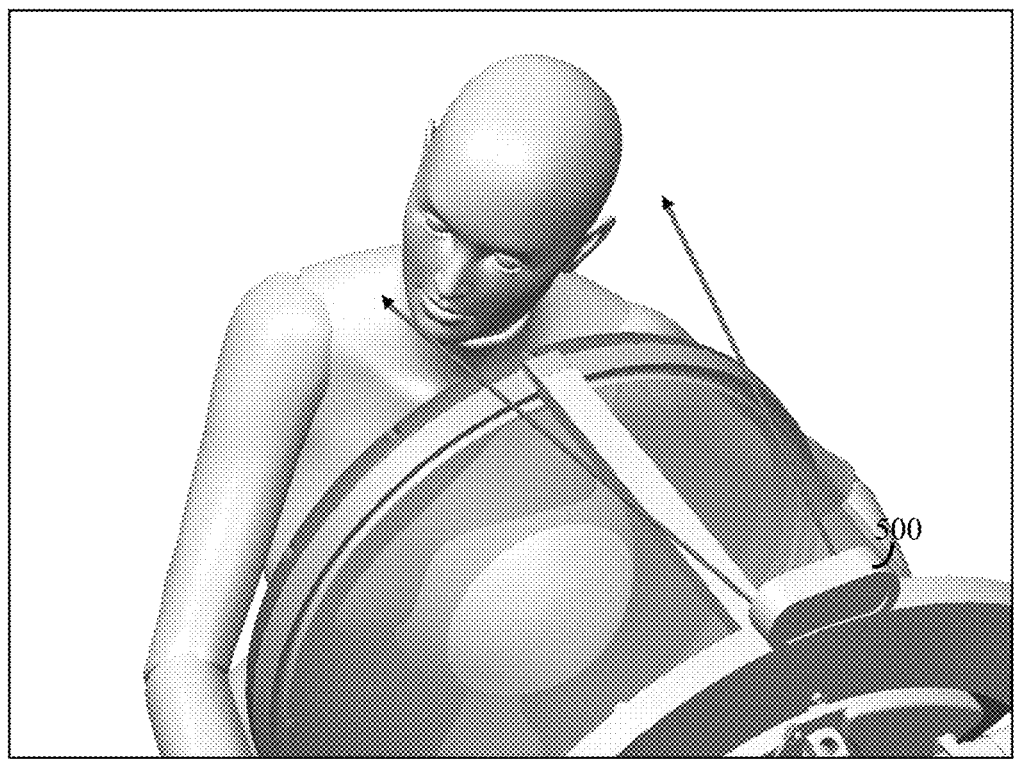
FIGS. 5A and 5B illustrate a perspective view and top view, respectively, of an example seated ultrasound tomography system incorporating breast laterality sensors.
Figure 5B:
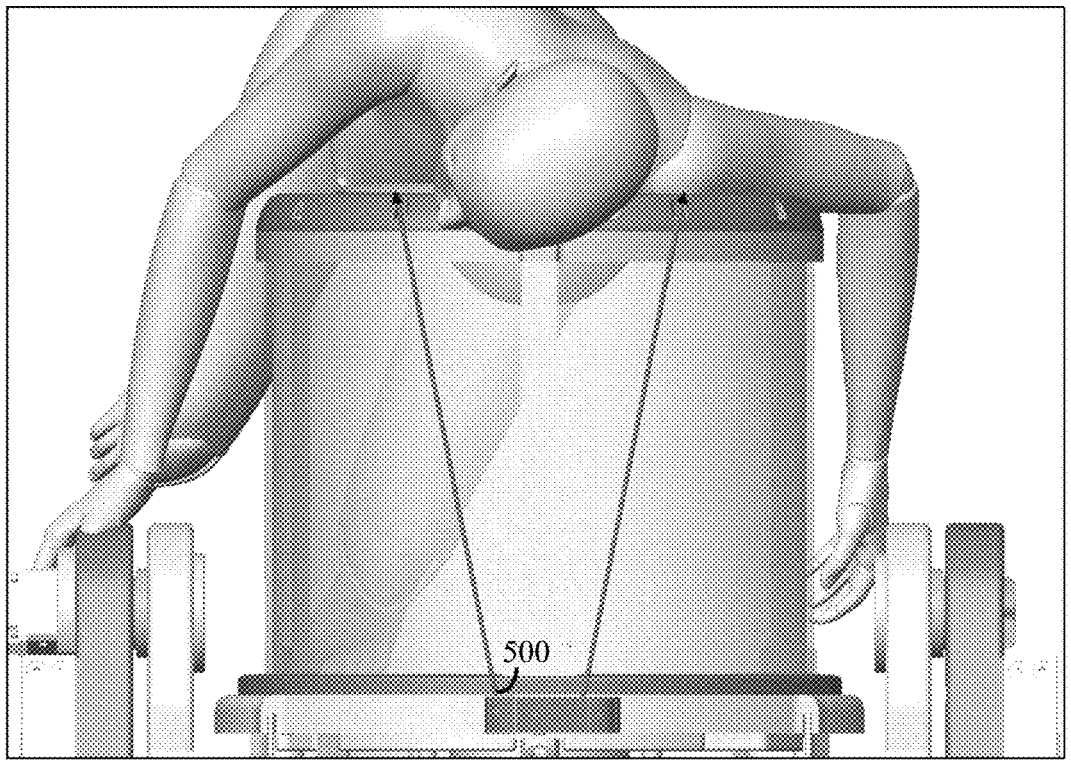

Placement for the above described sensors and systems may vary. One example non-force-sensitive sensor placement for a seated scanner is shown in FIGS. 5A and 5B. In particular, FIGS. 5A and 5B illustrate a perspective view and top view, respectively, of an example seated ultrasound tomography system incorporating breast laterality sensors. In the example illustration, a breast laterality sensor 500 involves an imaging device such as a thermal sensor or photo-based sensor (e.g., CCD or CMOS in visual or IR range). A primary requirement of placement of any such breast laterality sensor(s) 500 would be to have the patient area within the field of view of the device, which can be achieved by suitable placement of that device, depending on the transduction mechanism. Regardless of the size and weight of the patient, the position of patient at the time of scan will not be centered with respect to the center of the scanner. This relative difference in the position can be sensed as a difference in the transducer signal when comparing the right- and left-hand sides of the field of view. In some cases, two sensors are used—one angled to the left and the other angled to the right of the center (e.g., between 1 and 45 degrees from center). In some cases, one sensor is used where the sensor can rotate from an angle to a left of center to and angle to the right of center (and/or vice versa).

As an illustrative example, when using an image sensor as a breast laterality sensor, the pixels of the image sensor convert the charge from light striking the photodiode in each pixel to a voltage. The voltage from the pixels may be converted into digital information or simply used in the $V_{net}$ calculation in a similar manner as described with respect to FIG. 4.

For an example case where the voltage is converted into digital information, this digital information can be used to identify which of the two sensors has more body mass taking up the pixels. Images generated from the two sensors can be used to identify which of the two image sensors has more of the patient within a field of view. This may be accomplished by converting the images into binary (such as black and white by using gray threshold), removing background, calculating area of non-background pixels (e.g., those representing the patient), and determining which of the two images has higher area. If the image from the sensor directed to the left of center has a value indicating a higher area of pixels representing the patient, then it can be determined that the breast laterality is the right breast. Similarly, if the image from the sensor directed to the right of center has a value indicating a higher area of pixels representing the patient, then it can be determined that the breast laterality is the left breast.

For an example case where the $V_{net}$ calculation described with respect to FIG. 4 is used, the net difference between the voltage at the output of the image sensor directed to the left of center and the voltage at the output of the image sensor directed to the right of center (which may be the same sensor that is rotated or a different sensor) is calculated. The calculation can be $V_{net}=V_{left}-V_{right}$, where $V_{net}$ is the net difference voltage, $V_{left}$ and $V_{right}$ are the output voltages of the image sensor(s) directed to the left of center and the right of center, respectively. In this implementation, the absolute value of the voltage difference is not important for detection of laterality, it is the sign of the difference (sign + or sign −) which determines the decision (a corresponding indication of breast laterality). In some cases, instead of sign, a digital output, such as '0' or '1', can be provided. As also described with respect to FIG. 4, the net difference may be calculated as $V_{right}-V_{left}$ as long as the system understands how to interpret the output (e.g., can interpret the sign or the digital output as being the appropriate side).

Figure 6:
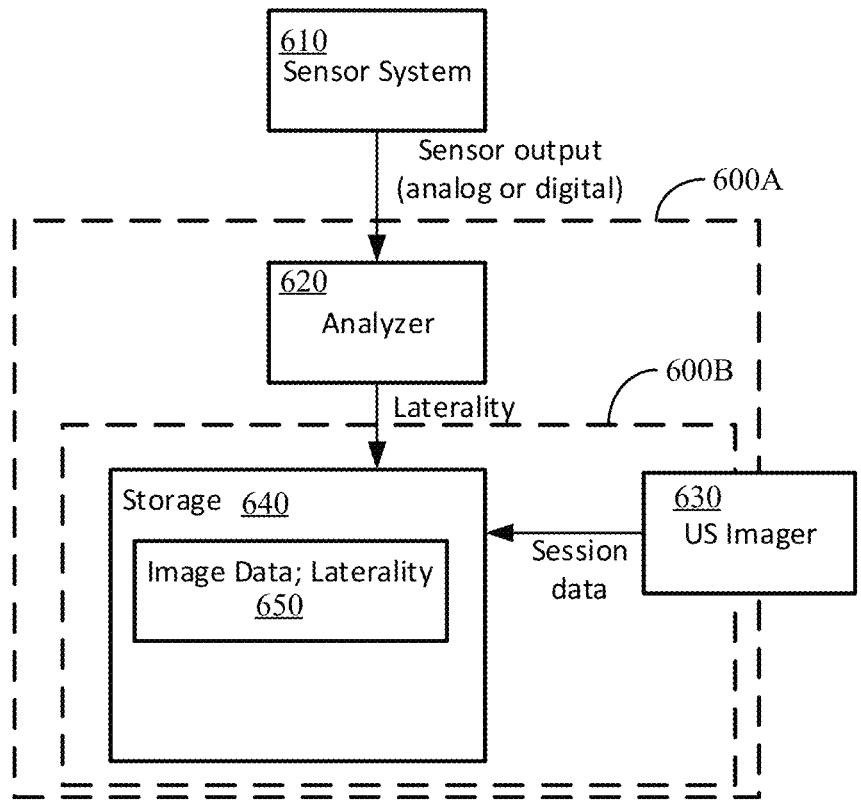
FIG. 6 shows a block diagram of a system for automatic laterality identification for ultrasound tomography systems.

FIG. 6 shows a block diagram of a system for automatic laterality identification for ultrasound tomography systems. Referring to FIG. 6, a sensor system 610 communicates with an analyzer 620 to provide sensor output, which can be analog or digital. The sensor system 610 can involve pressure or force sensors, image sensors, heat sensors, other sensors, or combinations thereof, for example such as described with respect to FIGS. 1, 2A-2C, 3A-3C, and 5A-5B. The analyzer 620 receives the output of the sensor system 610 and identifies the laterality. In some cases, the laterality is identified using process 400 described with respect to FIG. 4. Of course, any of the methods described herein may be used. The laterality identification can then be stored in a storage 640. The laterality identification can be presented to a user in a graphical user interface or used to confirm a manual entry of laterality that the user may have input via the graphical user interface of the ultrasound imaging software. Session data from an ultrasound imager system 630 can be stored in the storage 640 and have the appropriate laterality assigned as metadata to the image data from the session. The imaging data from the ultrasound imager system 630 and the automatically identified laterality can be stored in a database 650 (or other data structure) in the storage 640.

Aspects of the analyzer 620, ultrasound imager system 630, and the storage 640 may be embodied as one or more computing systems. For example, hardware and software for the ultrasound imaging software, analyzer, and storage can be embodied as computing system 600A. Alternatively, the analyzer 620 may be part of a standalone laterality detection system that includes the logic for performing certain calculations with respect to the output of the sensor system 610 and communicates wired or wirelessly with a computing system 600B providing the storage 640 and the ultrasound imaging software of the ultrasound imager system 630. In either case, the analyzer 620 can be wired or wirelessly coupled to the sensor system 610.

The analyzer can be implemented via hardware (e.g., FPGA) or software. When implemented as software, the analyzer can, when executed by a computing system, identify, using input received from the sensor system 610, whether a user has more of their body to a left side or a right side of the opening of a bed or seat-type apparatus; and assign a breast laterality of a right breast or a left breast to data generated by the ultrasound imaging based on whether the user has more of their body to the left side or the right side of the opening.

Example—Proof of Concept

A proof of concept design was implemented based on FIGS. 3A and 3C, where two force sensitive resistors—one as a left side laterality sensor and the other as a right-side laterality sensor—were connected as part of respective operational amplifier (op-amp) circuits. In the proof of concept, the force sensitive resistors were implemented by FSR-408 resistors from Interlink Electronics, Inc. Here, each force sensitive resistor had a single-zone active sensing area of 24" length and 0.25" width, and nominal thickness of 0.135". A total of n=5 volunteers were tested on the scanner bed. The voltage outputs of the two sensors were used to calculate the net voltage differences. The sign of the absolute value was used to indicate breast laterality, where a negative sign indicated a left laterality and a positive sign indicated a right laterality. In all instances, the force sensitive resistors correctly detected the breast laterality, and hence the detection accuracy was 100%.

Note that depending on the size and weight of the volunteer, the absolute voltage measurement can vary. There can be instances where the size/weight of the volunteer can result in equal pressure as measured by our current embodiment of the sensing mechanism wherein only two individual sensors are utilized. To overcome this concern, a network of multiple and smaller resistors can be potentially employed on each side to cover a larger area of the bed, such as shown in the scheme illustrated in FIG. 3B, and therefore to account for variation in the weight distribution on the scanner bed.

Example—Computing System

Figure 7:
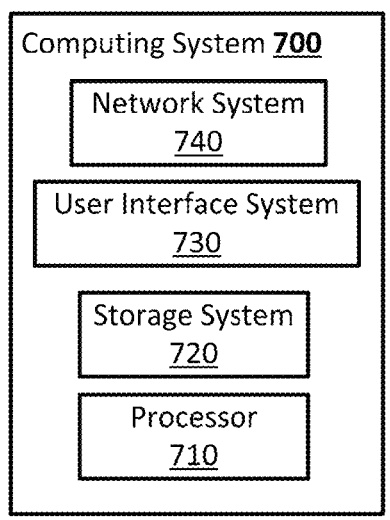
FIG. 7 illustrates an example computing system.

An example computing system is shown in FIG. 7. Computing system 700 may be used to implement computing system 600A and/or computing system 600B. Referring to FIG. 7, computing system 700 can include a hardware processor 710, storage system 720, user interface system 730, and network system 740.

Examples of hardware processor 710 include, but are not limited to, general purpose central processing units, application specific processors, and logic devices, as well as any other type of processing device, combinations, or variations thereof. Storage system 720 can provide storage 640; and can store any software used to implement analyzer 620 (of course some aspects of analyzer 620 may be implemented in hardware).

Storage system 720 can comprise any computer readable storage media readable by the processor 710 and capable of storing software and data. Storage system 720 may include volatile and nonvolatile, removable and non-removable media implemented in any method or technology for storage of information, such as computer readable instructions, data structures, program modules, or other data. Examples of storage media of storage system 720 include random access memory, read only memory, magnetic disks, optical disks, CDs, DVDs, flash memory, magnetic cassettes, magnetic tape, magnetic disk storage or other magnetic storage devices, or any other suitable storage media. As used herein, in no case is a "storage medium" a propagated signal or carrier wave (or other "transitory" media).

Storage system 720 may be implemented as a single storage device but may also be implemented across multiple storage devices or sub-systems co-located or distributed relative to each other. Storage system 720 may include additional elements, such as a controller, capable of communicating with processor 710.

The system 700 can further include user interface system 730, which may include input/output (I/O) devices and components that enable communication between a user and the system 700. Examples of I/O devices and components include, but are not limited to, a mouse, track pad, keyboard, a touch device for receiving a touch gesture from a user, a motion input device for detecting non-touch gestures and other motions by a user, a microphone for detecting speech, display screen(s), touchscreen, and speakers. Visual output may be depicted on a display in myriad ways, presenting graphical user interface elements, text, images, video, notifications, virtual buttons, virtual keyboards, or any other type of information capable of being depicted in visual form.

Network system 740 may include communications connections and devices that allow for communication with other computing systems over one or more communication networks (not shown). Examples of connections and devices that together allow for inter-system communication may include network interface cards, antennas, power amplifiers, RF circuitry, transceivers, and other communication circuitry. The connections and devices may communicate over communication media (such as metal, glass, air, or any other suitable communication media) to exchange communications with other computing systems or networks of systems.

It should be understood that the examples and embodiments described herein are for illustrative purposes only and that various modifications or changes in light thereof will be suggested to persons skilled in the art and are to be included within the spirit and purview of this application.

What is claimed is:

1. A system comprising:
    a scanner bed on which a patient is to be horizontally positioned for ultrasound imaging, the scanner bed comprising:
        a surface parallel to the ground, the surface having a fore end, an aft end, a left side, and a right side;
        an opening in the surface through which a patient's breast can be disposed, the opening positioned closer to the fore end than to the aft end and centered between the left side and the right side of the surface;
    a position sensor system comprising:
        a first set of force-sensitive resistors arranged to a left side of the opening and extending towards the aft end of the surface, wherein the first set of force-sensitive resistors includes a first network of multiple resistors;
        a second set of force-sensitive resistors arranged to a right side of the opening and extending towards the aft end of the surface, wherein the second set of force-sensitive resistors includes a second network of multiple resistors;
        a first op-amp circuit coupled to the first set of force-sensitive resistors; and
        a second op-amp circuit coupled to the second set of force-sensitive resistors,
        whereby an increase in force applied to the first set of force-sensitive resistors results in a decrease in resistance with a consequent increase in voltage at an output of the first op-amp circuit and an increase in force applied to the second set of force-sensitive resistors results in a decrease in resistance with a consequent increase in voltage at an output of the second op-amp circuit; and
    a computing system coupled to the position sensor system and having software stored thereon that, when executed by a processor of the computing system, directs the computing system to:
        identify, using the voltage at the output of the first op-amp circuit and the voltage at the output of the second op-amp circuit, whether the patient has more of their body to the left side or the right side of the opening; and
        assign a breast laterality of a right breast or a left breast to data generated by the ultrasound imaging based on whether the patient has more of their body to the left side or the right side of the opening.

2. The system of claim 1, wherein the software that directs the computing system to identify, using the voltage at the output of the first op-amp circuit and the voltage at the output of the second op-amp circuit, whether the patient has more of their body to the left side or the right side of the opening directs the computing system to:
    receive the voltage at the output of the first op-amp circuit and the right side voltage at the output of the second op-amp circuit;
    calculate a net voltage of a difference between the voltage at the output of the first op-amp circuit and the voltage at the output of the second op-amp circuit; and
    determine laterality according to the net voltage such that a positive net voltage identifies one side and a negative net voltage identifies the other side of the opening.

* * * * *